United States Patent
Reyes et al.

(10) Patent No.: US 10,420,870 B2
(45) Date of Patent: Sep. 24, 2019

(54) HEART RATE DETERMINATION BASED ON VAD CURRENT WAVEFORM

(71) Applicant: HeartWare, Inc., Miami Lakes, FL (US)

(72) Inventors: Carlos Reyes, Davie, FL (US); Fernando Casas, Miami Lakes, FL (US); Justin Wolman, Aventura, FL (US)

(73) Assignee: HeartWare, Inc., Miami Lakes, FL (US)

( * ) Notice: Subject to any disclaimer, the term of this patent is extended or adjusted under 35 U.S.C. 154(b) by 96 days.

(21) Appl. No.: 15/663,265

(22) Filed: Jul. 28, 2017

(65) Prior Publication Data

US 2018/0028737 A1 Feb. 1, 2018

Related U.S. Application Data

(60) Provisional application No. 62/369,326, filed on Aug. 1, 2016.

(51) Int. Cl.
*A61M 1/00* (2006.01)
*A61M 1/12* (2006.01)
(Continued)

(52) U.S. Cl.
CPC ............. *A61M 1/122* (2014.02); *A61B 5/029* (2013.01); *A61B 5/02438* (2013.01);
(Continued)

(58) Field of Classification Search
CPC ............. A61M 1/10–127; A61B 5/024; A61B 5/02438
See application file for complete search history.

(56) References Cited

U.S. PATENT DOCUMENTS 8,512,013 B2    8/2013 LaRose et al.
2014/0323796 A1* 10/2014 Medvedev .......... A61M 1/1086
                                                     600/17

FOREIGN PATENT DOCUMENTS

WO        200172352 A2   10/2001
WO       2014179271 A2   11/2014

OTHER PUBLICATIONS

International Search Report and Written Opinion dated Mar. 1, 2018, for corresponding International Application No. PCT/US2017/044459; International Filing Date: Jul. 28, 2017 consisting of 12-pages.

* cited by examiner

*Primary Examiner* — Eric D. Bertram
(74) *Attorney, Agent, or Firm* — Christopher & Weisberg, P.A.

(57) ABSTRACT

The present disclosure provides for methods and systems for determining heart rate of a patient. Based on motor current signals of a ventricular assist device (VAD), each of first, second and third events in the measured current signal may be detected, the first event being indicative of a rise or fall in the current signal, the second event being indicative of a rise or fall in the current signal in the opposite direction as the first event, and the third event being indicative of a rise or fall in the current signal in the same direction as the first event. A timer counter may be initiated upon detection of the first event, and an elapsed time may be measured upon detection of the third event. Heart rate may be determined based on the elapsed time of the timer counter.

10 Claims, 1 Drawing Sheet

(51) Int. Cl.
*A61B 5/029* (2006.01)
*A61M 1/10* (2006.01)
*A61B 5/024* (2006.01)
*A61B 5/00* (2006.01)

(52) U.S. Cl.
CPC ......... *A61M 1/1086* (2013.01); *A61B 5/7235* (2013.01); *A61M 1/1029* (2014.02)

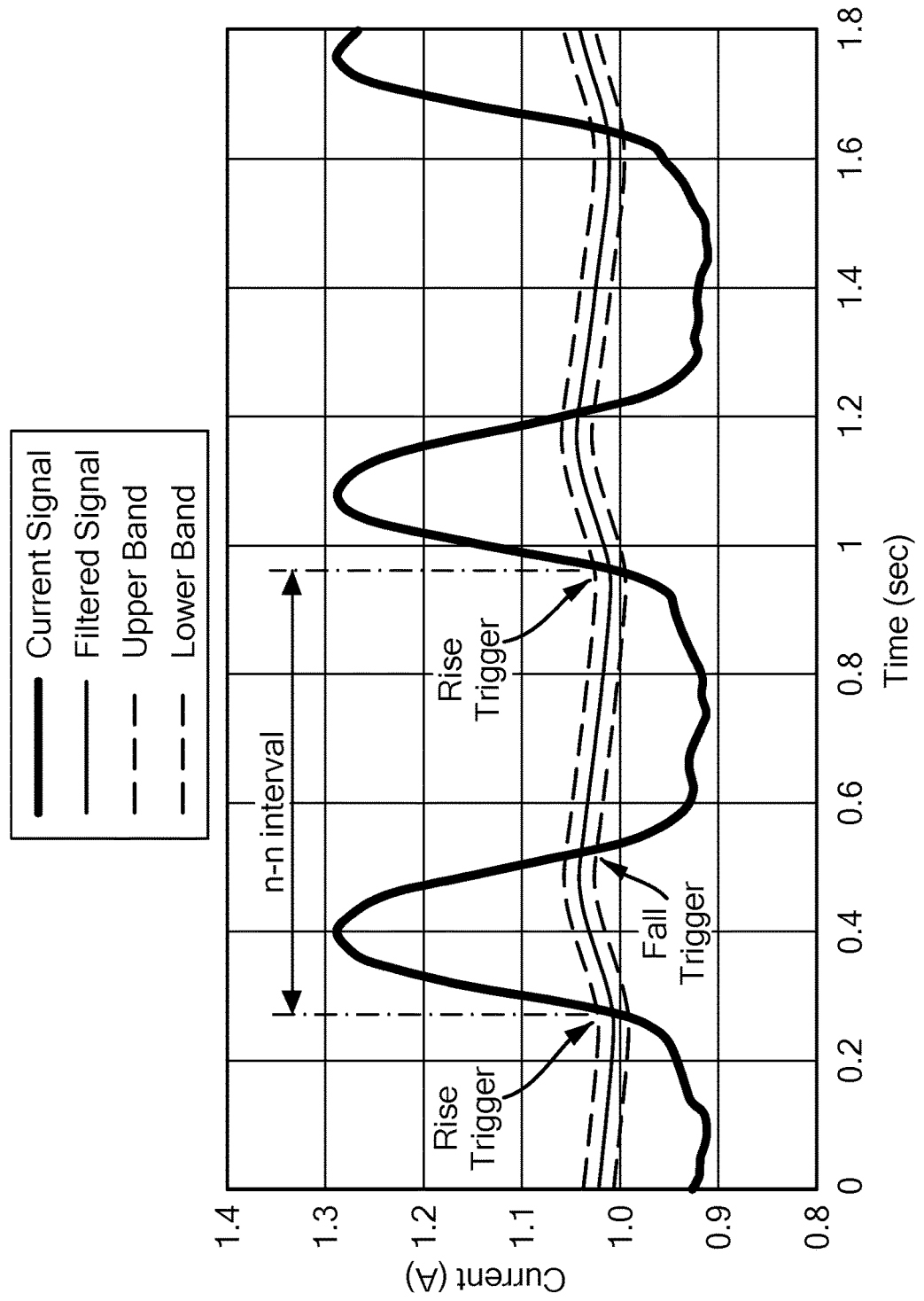

HEART RATE DETERMINATION BASED ON VAD CURRENT WAVEFORM

CROSS-REFERENCE TO RELATED APPLICATION

This application is related to and claims priority to U.S. Provisional Patent Application Ser. No. 62/369,326, filed Aug. 1, 2016, entitled HEART RATE DETERMINATION BASED ON VAD CURRENT WAVEFORM, the entirety of which is incorporated herein by reference.

STATEMENT REGARDING FEDERALLY SPONSORED RESEARCH OR DEVELOPMENT n/a

TECHNICAL FIELD

The present invention relates to a method and system for determining a patient's heart rate based on a parameter of an implantable blood pump.

BACKGROUND

Implantable blood pumps may be used to provide assistance to patients with late stage heart disease. Blood pumps operate by receiving blood from a patient's vascular system and impelling the blood back into the patient's vascular system. By adding momentum and pressure to the patient's blood flow, blood pumps may augment or replace the pumping action of the heart. For example, a blood pump may be configured as ventricular assist device or "VAD."

A VAD is a device which is used to assist the heart of a mammalian subject such as a human patient. A typical VAD includes a pump which is implanted in the body of the subject. The pump typically has an inlet connected to a source of blood to be circulated, and an outlet connected to an artery. Most typically, the inlet of the pump is connected to the interior of the left ventricle and the outlet of the pump is connected to the aorta, so that the pump operates in parallel with the left ventricle to impel blood into the aorta. The pump may be a miniature rotary impeller pump having an impeller disposed in a pump housing and driven in rotation by a small electric motor which may be closely integrated with the pump. The motor in turn typically is powered by an implantable power source such as a storage battery with an arrangement for charging the battery from an external power source. The VAD typically includes a control system which controls operation of the power source so as to drive the impeller at a set rotational speed and thus provide constant pumping action.

VADs can be used to assist the heart of subjects suffering from conditions which impair the pumping ability of the heart. Such assistance can be provided permanently, or while the subject awaits a suitable heart transplant. In other cases, the assistance provided by the VAD allows the heart to heal.

In many circumstances, it is desirable to detect and monitor a heart rate of the patient. This may be accomplished using electrocardiogram (ECG) signals to detect a sinus rhythm of the patient's heart. Since the patient's cardiac cycle is simply the inverse of the heart rate, the ECG signals may further be used to detect and monitor a heart rate of the patient. However, heart rate monitoring using ECG signals requires the patient to be equipped with ECG electrodes.

Therefore, it is desirable to provide a method and system for determining heart rate using the VAD circuitry, without reliance on ECG data.

SUMMARY

The present invention advantageously provides a system of one or more computers configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

One general aspect includes a method of determining heart rate of a patient having an implantable blood pump, including: measuring a motor current signal of the implantable blood pump, the implantable blood pump being in fluid communication with a ventricle of the patient's heart. The method of determining heart rate also includes detecting a first event in the measured current signal, the first event being indicative of one from the group including of a rise in the current signal and a fall in the current signal. The method of determining heart rate also includes initiating a timer counter when detecting the first event. The method of determining heart rate also includes detecting a second event in the measured current signal, the second event being indicative of one from the group including of a rise in the current signal and a fall in the current signal in the opposite direction as the first event. The method of determining heart rate also includes detecting a third event in the measured current signal, the third event being indicative of one from the group including of a rise in the current signal and a fall in the current signal in the same direction as the first event. The method of determining heart rate also includes measuring an elapsed time of the timer counter when detecting the third event. The method of determining heart rate also includes determining the heart rate of the patient based on the elapsed time of the timer counter. Other embodiments of this aspect include corresponding computer systems, apparatus, and computer programs recorded on one or more computer storage devices, each configured to perform the actions of the methods.

Implementations may include one or more of the following features: the method where detecting the second event is initiated after the first event is detected, and where detecting the third event is initiated after the second event is detected. The method where the first event and the third event are rises in current signal and the second event is a fall in current signal. The method where the first event and the third event are falls in current signal and the second event is a rise in current signal. The method where the motor current signal is unfiltered, and where the method further includes filtering the motor current signal to create a filtered signal, and where the first, second, and third events are detected using a combination of the unfiltered current signal and the filtered signal. The method where detecting the rise in current signal occurs when the unfiltered current signal exceeds the filtered current signal by a first predetermined amount, and where detecting the fall in current signal occurs when the unfiltered current signal is less than the filtered current signal by a second predetermined amount. The method where the first predetermined amount and the second predetermined amount are equal. The method where the filtered signal is a running average of the motor current signal. The method where detecting the first, second and third events is repeatedly performed, and where the method includes measuring a plurality of elapsed times, and where the heart rate is determined based on an average of the plurality of elapsed times. The method further includes initiating a second counter timer when detecting the second event. The method may also include detecting of a fourth event in the measured current signal after detecting the third event, the fourth event being indicative of one from the group including of a rise in the current signal and a fall in the current signal in the same direction as the second event. The method may also include measuring an elapsed time of the second timer counter when detecting the fourth event. The method further includes repeatedly determining the heart rate to obtain a plurality of heart rate values over a predetermined amount of time. The method may also include determining a statistical variability of the plurality of heart rate values indicative of heart rate variability. The method where determining a statistical variability of the plurality of heart rate values includes determining a standard deviation of the heart rate values. Implementations of the described techniques may include hardware, a method or process, or computer software on a computer-accessible medium.

One general aspect includes a control circuit for determining heart rate of a patient, the control circuit including: memory for storing instructions; and a processor for executing the instructions stored in the memory, the processor is configured to communicate with a ventricular assist device to provide control signals to the ventricular assist device and to sense a motor current of the ventricular assist device, and is further configured to detect a first event of the patient's cardiac cycle from the sensed motor current, the first event indicative of a beginning of one from the group including of systole and diastole. The control circuit further detects a second event of the patient's cardiac cycle from the sensed motor current, the second event indicative of a beginning of the other from the group including of systole and diastole. The control circuit further detects a third event of the patient's cardiac cycle from the sensed motor current, the third event indicative of a beginning of the same one from the group including of systole and diastole as the first event. The control circuit also measures a duration of time between the first and third events. The control circuit also determines the patient's heart rate based on the measured duration of time. Other embodiments of this aspect include corresponding computer systems, apparatus, and computer programs recorded on one or more computer storage devices, each configured to perform the actions of the methods.

Implementations may include one or more of the following features: the control circuit where the first and third events are rises in the sensed motor current and the second event is a fall in the sensed motor current. The control circuit where the first and third events are falls in the sensed motor current, and the second event is a rise in sensed motor current. The control circuit where the sensed motor current is an unfiltered current signal, and where the control circuit further includes a filter in communication with processor for filtering the motor current signal, and, and where the processor is configured to detect the first, second, and third events using a combination of the unfiltered current signal and the filtered signal. The control circuit where the processor is configured to detect a rise in the sensed motor current when the unfiltered current signal exceeds the filtered current signal by a preset amount, and where the processor is configured to detect a fall in the sensed motor current when the unfiltered current signal is less than the filtered current signal by the preset amount. The control circuit where the filtered signal is a running average of the sensed motor current. The control circuit where the processor is further configured to, after detection of the third event, detect a fourth event in the sensed motor current, the fourth event indicative of a beginning of the same one from the group including of systole and diastole as the second event. The control circuit may measure a duration of time between the second and fourth events. The control circuit may also determine the patient's heart rate based on the measured duration of time between the second and fourth events. Implementations of the described techniques may include hardware, a method or process, or computer software on a computer-accessible medium.

One general aspect includes a ventricular assist device including a control circuit including a memory for storing instructions and a processor for executing the instructions stored in the memory, the processor is configured to communicate with a ventricular assist device to provide control signals to the ventricular assist device and to sense a motor current of the ventricular assist device, and is further configured to: detect a first event of the patient's cardiac cycle from the sensed motor current, the first event indicative of a beginning of one from the group consisting of systole and diastole; detect a second event of the patient's cardiac cycle from the sensed motor current, the second event indicative of a beginning of the other from the group consisting of systole and diastole; detect a third event of the patient's cardiac cycle from the sensed motor current, the third event indicative of a beginning of the same one from the group consisting of systole and diastole as the first event; measure a duration of time between the first and third events; and determine the patient's heart rate based on the measured duration of time. The ventricular assist device also detects a first event of the patient's cardiac cycle from the sensed motor current, the first event indicative of a beginning of one from the group including of systole and diastole. The ventricular assist device also detects a second event of the patient's cardiac cycle from the sensed motor current, the second event indicative of a beginning of the other from the group including of systole and diastole. The ventricular assist device also detects a third event of the patient's cardiac cycle from the sensed motor current, the third event indicative of a beginning of the same one from the group including of systole and diastole as the first event. The ventricular assist device also measures a duration of time between the first and third events. The ventricular assist device also determines a patient's heart rate based on the measured duration of time. The ventricular assist device also includes a rotary pump configured to be implantable in fluid communication with the patient's heart to assist blood flow from the heart. The ventricular assist device also includes a pump drive circuit in communication with the control circuit and the rotary pump, the pump drive circuit configured to supply power to the pump and control speed of the pump in response to control signals received from the control circuit. Other embodiments of this aspect include corresponding computer systems, apparatus, and computer programs recorded on one or more computer storage devices, each configured to perform the actions of the methods.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 1 is a graph showing measured current drawn by an exemplary implanted ventricular assist device over time in comparing a filtered signal to an unfiltered signal.

DETAILED DESCRIPTION

The present application provides for determination of a patient's heart rate using VAD motor current. The present application is applicable to any VAD known to have a single valued (e.g., linear, increasing, decreasing) relationship between pump flow and motor current across operational ranges of flow and current for the VAD, such as the HVAD® Pump manufactured by HeartWare Inc. in Miami Lakes, Fla., USA. The HVAD® Pump is further discussed in commonly owned U.S. Pat. No. 8,512,013, as well as the commonly owned and concurrently filed U.S. Provisional Patent Application No. 62/369,528 entitled "VAD with Aortic Valve Opening Detection," the applications of which are hereby incorporated herein in their entirety.

In a VAD in fluid communication with a patient's heart, every heartbeat causes changes in the pressure differential across the VAD. More specifically, if the VAD is operating in a non-pulsatile mode and maintains a generally constant flow rate of blood over the course of a cardiac cycle, contraction of the heart causes an increase of pressure at an inlet of the pump. The increase of pressure affecting the overall differential pressure between the inlet and outlet of the pump. Such change in differential pressure corresponds with a measurable change of flow, which may be observed via fluctuations in VAD motor current. Specifically, the VAD controller may be in communication with one or more current sensors adapted to sense fluctuations in current drawn by the VAD motor to maintain the constant speed of an impeller of the VAD. These fluctuations in motor current have approximately the same periodicity as the patient's cardiac cycle. Thus, analysis of the fluctuations in motor current may be used to produce a heart rate determination.

Referring now to FIG. 1, a measured motor current signal (thick solid line) is sensed by a current sensor in communication with the VAD motor. This motor current signal is an unfiltered signal. A filtered motor current signal is also shown in FIG. 1. The filter may either be included in or connected to the VAD control circuit. In one example, the filter may be low pass filter, such as a running average or weighted running average (e.g., exponential running average) of VAD motor current. The number of cardiac cycles averaged by the filter may vary depending on the patient's heart rate.

Fluctuations in motor current signal may be monitored based on rises and falls in the motor current. A rise in motor current may indicate the beginning of systole for the patient's cardiac cycle, whereas a fall in motor current may indicate the beginning of diastole. Thus, by tracking a rise, subsequent fall, and subsequent rise in motor current, it may be determined that the patient's heart has completed one full cardiac cycle, beginning with systole and ending with diastole. Alternatively, a complete cardiac cycle beginning with diastole and ending with systole may be identified by tracking a rise, subsequent fall, and subsequent rise in motor current.

Rises and falls in motor current may be triggered by an event detected in the motor current, such as the unfiltered current signal crossing the filtered current signal (also referred to as a "zero-crossing point"). In the example of FIG. 1, instead of directly using the zero-crossing point between the unfiltered and filtered current signals, a rise or fall is considered to occur only after the unfiltered current signal crosses the filtered current signal and exceeds (for rising) or is less than (for falling) a preset amount (referred to as "upper band" and "lower band" in FIG. 1). In the example of FIG. 1 the preset amount is the same for the upper and lower bands. However, in other examples, the upper and lower bands may be independently preset at different values. For example, as shown in FIG. 1, the "n-n" interval represents the time between the detecting a first event in the measured current signal, the first event being indicative of one from the group consisting of a rise in the current signal and a fall in the current signal, and between detecting a third event in the measured current signal, the third event being indicative of one from the group consisting of a rise in the current signal and a fall in the current signal in the same direction as the first event. In between the first and third events is when detecting a second event occurs, the second event being indicative of one from the group consisting of a rise in the current signal and a fall in the current signal in the opposite direction as the first event.

Heart rate may be determined based on a calculation of an amount of time elapsed during one or more complete cardiac cycles of the patient. Elapsed time may be tracked using a timer either included in or connected to the VAD control circuit. Upon detection of the first event (either a rise or fall in the motor signal), the timer is started. Also upon detection of the first event, the control circuit begins searching for and detects the subsequent second event opposite the first event (a fall if the first event is a rise, or a rise if the first event is a fall). Upon detection of the second event, the control circuit begins searching for and detects the subsequent third event the same as the first event (a rise if the first event is a rise, or a fall if the first event is a fall). Upon detection of the third event, the elapsed time is measured. The measured elapsed time equals the period of the patient's cardiac cycle. Thus, the heart rate of the patient may be determined by taking the inverse of the measured elapsed time.

In the above example, heart rate is determined based on a single cardiac cycle. However, in other examples, heart rate may be determined based on a combination of multiple cardiac cycles. For instance, the above heart rate determination may be performed any discrete number of times, and the results of each determination may be averaged to derive an average heart rate. Upon detection of the third event, the elapsed time is measured. The measured elapsed time equals the period of the patient's cardiac cycle. Thus, the heart rate of the patient may be determined by taking the inverse of the measured elapsed time.

In yet further examples, multiple heart rate determinations may be performed simultaneously using a plurality of timers. For instance, the second event of one heart rate determination may simultaneously function as the first event of another heart rate determination. In such an instance, the third event of the first heart rate determination may also function as the second event of the second heart rate determination. Upon detection of the third event, the control circuit may begin searching for and detects a subsequent fourth event the same as the second event (a rise if the second event is a rise, or a fall if the second event is a fall), which functions as the third event of the second heart rate determination. A first timer may measure elapsed time between the first and third events, whereas a second timer measures elapsed time between the second and fourth events. In this respect, the control circuit may be capable of performing approximately two heart rate determinations per cardiac cycle of the patient: one determination beginning with systole and ending with diastole, and another determination beginning with diastole and ending with systole.

In those examples where multiple heart rate determinations are performed, the determinations may be stored in memory (e.g., a heart rate log file) for further evaluation, either by a clinician or through an automated process conducted by the VAD controller or an external processor. One such evaluation considers variability of the determined heart rate values over time. For instance, heart rate values may be repeatedly determined using any of the above described procedures for a predetermined amount of time (e.g., about 5 minutes). Then, descriptive statistics are obtained for the heart rate values determined over the predetermined amount of time. For example, a standard deviation of the heart rate values may be determined. In some instances, once the descriptive statistics are obtained, the determined heart rate values stored in memory may be cleared, and the process may be repeated.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

What is claimed is:

1. A method of determining heart rate of a patient having an implantable blood pump, comprising:
   measuring a motor current signal of the implantable blood pump, the implantable blood pump being in fluid communication with a ventricle of the patient's heart;
   detecting a first event in the measured current signal, the first event being indicative of one from the group consisting of a rise in the current signal and a fall in the current signal;
   initiating a timer counter when detecting the first event;
   detecting a second event in the measured current signal, the second event being indicative of one from the group consisting of a rise in the current signal and a fall in the current signal in the opposite direction as the first event;
   detecting a third event in the measured current signal, the third event being indicative of one from the group consisting of a rise in the current signal and a fall in the current signal in the same direction as the first event;
   measuring an elapsed time of the timer counter when detecting the third event;
   filtering the motor current signal to create a filtered signal, and having the first, second, and third events be detected using a combination of the unfiltered motor current signal and the filtered signal; and
   determining the heart rate of the patient based on the elapsed time of the timer counter.

2. The method of claim 1, wherein detecting the second event is initiated after the first event is detected, and wherein detecting the third event is initiated after the second event is detected.

3. The method of claim 1, wherein the first event and the third event are rises in current signal and the second event is a fall in current signal.

4. The method of claim 1, wherein detecting the rise in current signal occurs when the unfiltered current signal exceeds the filtered current signal by a first predetermined amount, and wherein detecting the fall in current signal occurs when the unfiltered current signal is less than the filtered current signal by a second predetermined amount.

5. The method of claim 4, wherein the first predetermined amount and the second predetermined amount are equal.

6. The method of claim 1, wherein the filtered signal is a running average of the motor current signal.

7. The method of claim 1, wherein detecting the first, second and third events is repeatedly performed, and wherein the method includes measuring a plurality of elapsed times, and wherein the heart rate is determined based on an average of the plurality of elapsed times.

8. The method of claim 1, further comprising:
   initiating a second counter timer when detecting the second event;
   detecting of a fourth event in the measured current signal after detecting the third event, the fourth event being indicative of one from the group consisting of a rise in the current signal and a fall in the current signal in the same direction as the second event; and
   measuring an elapsed time of the second timer counter when detecting the fourth event.

9. The method of claim 1, further comprising:
   repeatedly determining the heart rate to obtain a plurality of heart rate values over a predetermined amount of time; and
   determining a statistical variability of the plurality of heart rate values indicative of heart rate variability.

10. The method of claim 9, wherein determining a statistical variability of the plurality of heart rate values comprises determining a standard deviation of the heart rate values.

* * * * *